(12) United States Patent
Wasser et al.

(10) Patent No.: US 6,372,462 B2
(45) Date of Patent: Apr. 16, 2002

(54) PROCESS FOR PRODUCING, METHODS AND COMPOSITIONS OF CHOLESTEROL LOWERING AGENTS FROM HIGHER BASIDIOMYCETES MUSHROOMS

(75) Inventors: Solomon P. Wasser, Haifa (IL); Sergey V. Reshetnikov, Kiev (UA)

(73) Assignee: MedMyco Ltd., Haifa (IL)

( * ) Notice: Subject to any disclaimer, the term of this patent is extended or adjusted under 35 U.S.C. 154(b) by 0 days.

(21) Appl. No.: 09/419,205

(22) Filed: Oct. 15, 1999

(51) Int. Cl.[7] .................................................. C12P 1/02

(52) U.S. Cl. ................. 435/171; 435/256.8; 435/254.1; 424/195.15

(58) Field of Search ........................... 435/256.8, 254.1, 435/171; 424/195.15

(56) References Cited

U.S. PATENT DOCUMENTS

| | | | |
|---|---|---|---|
| 3,716,579 A | * | 2/1973 | Knauseder et al. |
| 4,231,938 A | | 11/1980 | Monaghan et al. |
| 4,369,253 A | * | 1/1983 | Takita et al. |
| 5,712,130 A | | 1/1998 | Hajko et al. |

FOREIGN PATENT DOCUMENTS

EP     877089 A1    11/1998

OTHER PUBLICATIONS

Hadar et al. Applied and Environmental Microbiology (1986), vol. 51, No. 6, p. 1352.*
ATCC catalog; Filamentous Fungi, 19th edition, Jong et al., eds. p. 424, entry #90212, 1996.*
Microbiology Letters III: 333–338, 1993, vol. 113 Bobek et al. 1996, Närung: 222–224.

* cited by examiner

Primary Examiner—Francisco Prats
Assistant Examiner—Susan D. Coe
(74) Attorney, Agent, or Firm—Rashida A. Karmali

(57) ABSTRACT

The present invention describes new and distinct strains of higher Basidiomycetes mushrooms, and a process for growing them in submerged culture. Specifically, the new strains of species of the genus Pleurotus offer superior yields of mushroom biomass and concentrations of biologically active compounds, for example, cholesterol-lowering compounds, lectins, proteins, essential amino acids, vitamins or polysaccharides. The process includes use of defined media and a simple one-step procedure of separating the lovastatin-containing nutriceuticals from culture broth.

4 Claims, 12 Drawing Sheets

PROCESS FOR PRODUCING, METHODS AND COMPOSITIONS OF CHOLESTEROL LOWERING AGENTS FROM HIGHER BASIDIOMYCETES MUSHROOMS

FIELD OF THE INVENTION

The present invention is directed to a process for culturing a variety of higher Basidiomycetes mushrooms to produce superior yields of biologically active nutriceuticals. The nutriceutical agents are isolated by a simple one-step process, and are formulated for use as dietary supplements to achieve normal human bodily functions in general, and to control particular abnormal factors, for example, hypercholesterolemia, in particular.

BACKGROUND OF THE INVENTION

Mushrooms or macrofungi with distinctive fruiting bodies of sufficient size to be seen with the naked eye, include about 10,000 species of varying degrees of edibility. Approximately 100 species have been tested for cultivation and only seven to eight have been cultivated on an industrial scale. The world production of cultivated edible mushrooms in 1994 was estimated to be about five million tons and was valued at about ten billion US dollars. The most popular species of cultivated edible mushrooms include *Agaricus bisporus* (J. Lge) Imbach, *A. bitorquis* (Quél.) Sacc., *Lentinus edodes* (Berk.) Sing, Pleurotus spp., Auricularia spp., *Volvariella volvacea* (Fr.) Sing., *Flammulina velutipes* (Fr.) Sing, *Tremella fuciformis* Berk., *Hypsizygus marmoreus* (Peck) Bigel., *Pholita nameko* (T. Ito) S. Ito et Imai, *Grifola frondosa* (Dicks.: Fr.) S. F. Gray, *Hericium erinaceus* (Bull.: Fr.) Pers., *Dictyophora indusiata* (Vent.: Pers.) Fischer, *Stropharia rugosoannulata* Farl. apud Murr., *Lepista nuda* (Bull.: Fr.) Cooke, *Agrocybe aegerita* (Brig.) Sing.

The cultivation of fruiting bodies of mushrooms deals with living organisms, for example, the mushroom itself and other microorganisms which may either be harmful or beneficial. Therefore, the methods employed in mushroom cultivation require modifications depending upon the region being cultivated, substrates available, environmental conditions and species of microorganisms encountered.

The cultivation of mushrooms for fruiting bodies production is a long-term process needed from one to several months for the first fruiting bodies to appear. Moreover, in the case with *Pleurotus ostreatus* it is known that lovastatin is concentrated presumably in the lamella and basidiospores but not in the stipe or cap tissue, and its amount depends on fruiting body size, age, and substrate composition. Therefore, the submerged culturing of lovastatin producers allows production of the end product which has a constant composition, in a short period, by using controlled conditions such as ecologically pure culture medium of defined composition.

Lovastatin (=mevinolin) (=MSD 803), is a useful hypocholesterolemic pharmacological agent of natural origin. It is a competitive inhibitor of 3-hydroxy-3-methyl-glutaryl-coenzyme A reductase (HMG CoA reductase), the key enzyme in cholesterol metabolism. Monaghan et al, U.S. Pat. No. 4,231,938. The best producers of lovastatin are different strains of *Aspergillus terreus* a common contaminant mold on food, which contains several toxic substances including terrein, patulin, citrinin, and citreoviridin. As a result, lovastatin isolated from Aspergillus requires an extensive purification process involving extraction of lovastatin from the culture broth with ethyl acetate or XAD-2 resin and subsequent steps of concentration, washing, reconcentration, and recrystallization. U.S. Pat. No. 4,231,938. Alternate processes for isolation of lovastatin include use of different resins or less toxic solvent, such as butyl acetate in the first step of extraction of the culture broth. The culture broth which is extracted includes both the culture medium and the cell mass. For example, even for strains of Pleurotus grown in submerged cultures, lovastatin was extracted from the culture broth. DE 4,402,259 and Gunde-Cimerman et al, 1993, Microbiology Letters III: 203–206.

In general, the efficiency of lovastatin production is determined by the amount of lovastatin produced by the various fungi strains together with the efficiency of the extraction procedure employed. The Aspergillus strains are more productive than the Pleurotus strains in producing greater amounts of lovastatin. U.S. Pat. No. 4,231,938. However, the Aspergillus strains produce a wide range of toxic substances besides the cholesterol lowering lovastatin, and this requires complex and additional extraction and purification procedures to obtain lovastatin. Not only are these procedures more expensive but they require use of large numbers of solvents, which in turn are toxic e.g. benzene, toluene, acetonitrile, or ethyl acetate. Hence, working with these solvents endangers the health of persons involved, and requires multi-step purification procedures. Accordingly, there is need for methods to produce cholesterol-lowering compounds with a high activity, preferably from sources that are not toxic, and by using simple, rapid and inexpensive manufacturing processes. Moreover, different cholesterol-lowering compounds have varying degrees of activity. The process of the present invention involves production of a cholesterol lowering compounds from edible Basidiomycetes mushrooms grown in submerged cultures. The mycelium is grown on nutrient media especially formulated to produce high yields of the cholesterol-lowering compound and other nutrients.

SUMMARY OF THE INVENTION

The present invention relates to cultivation in submerged culture containing defined nutrient media of a mycelium of the edible Basidiomycetes mushrooms comprising *Pleurotus ostreatus, Pleurotus eryngii* var. *ferulae, Hypsizygus marmoreus, Lepista nuda, Pleurotus cystidiosus, P. dijamor, P. pulmonarius, P. salignus, Grifola frondosa,* and *Hericium erinaeus*.

In a first aspect, the invention provides a method of cultivating submerged cultures of one or more Basidiomycetes mushrooms having the trait to produce one or more substances having hypocholesterolemic activity. The use of the nutrient media of the invention, comprising a saccharide containing glucose in the molecule, an organic or mineral source of nitrogen and a variety of salts, is especially suited to enhance the production of the cholesterol-lowering nutrients and other essential nutrients.

In the second aspect, the invention provides a method to concentrate the hypocholesterolemic compound mainly in the mushroom cells thus enabling the simple separation of the edible biomass from the fermentation broth, thereby requiring no further extraction, concentration, purification or complex separation procedures. The simple separation of the edible Basidiomycetes from the culture broth of the present invention is followed by the drying of the final nutriceutical product at 40–45° C.

In accordance with the invention, compositions including a cholesterol-lowering compound are described, which, when orally consumed or ingested, inhibit the biosynthesis of mevalonic acid by inhibition of 3-hydroxy-3- methylglutaryl A reductase coenzyme (HMG-COA reductase, E.C.1.1.1.34) and thus reducing cholesterol levels in blood of a mammal. The preventive and/or treatment method of the invention therefore involves reduction of risk posed by elevated cholesterol in subjects at high risk of having cardiovascular disease.

The present invention can provide methods and compositions including nutriceutical components generally beneficial for promoting health, for example, lovastatin, polysaccharides, proteins and essential amino acids, vitamins, fiber, fatty acids, or minerals.

Still other objects and advantages of the invention will in part be obvious and will in part be apparent from the specification.

DETAILED DESCRIPTION OF THE INVENTION

Figure 1:
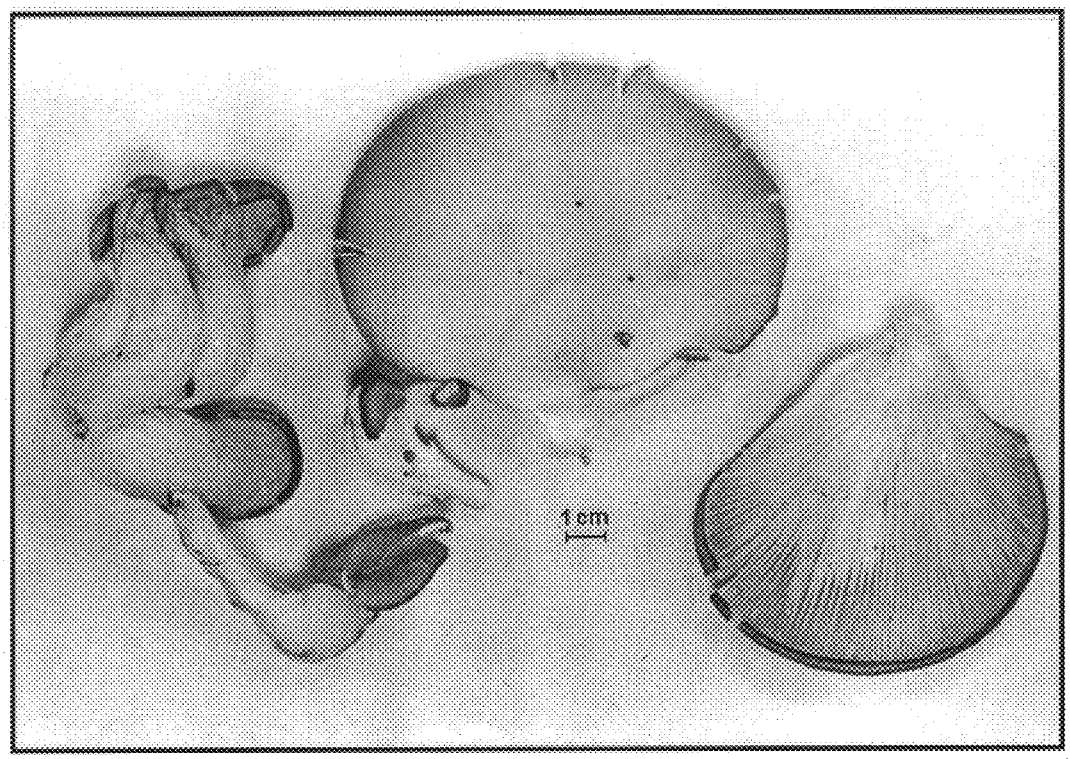
FIG. 1 shows a top view of the cultivated mushroom *Pleurotus ostreatus* CBS 101937 fruiting bodies.
Figure 2:
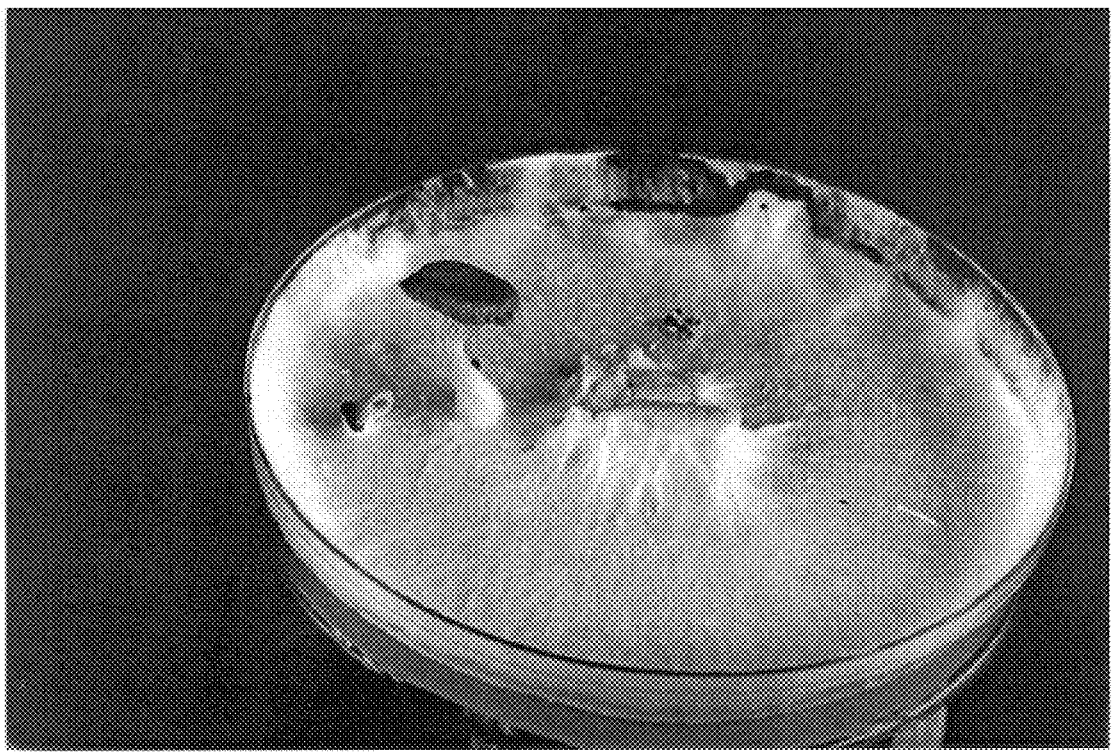
FIG. 2 shows a view of *Pleurotus ostreatus* CBS 101937 fruiting in the petri dish with malt agar medium.
Figure 3:
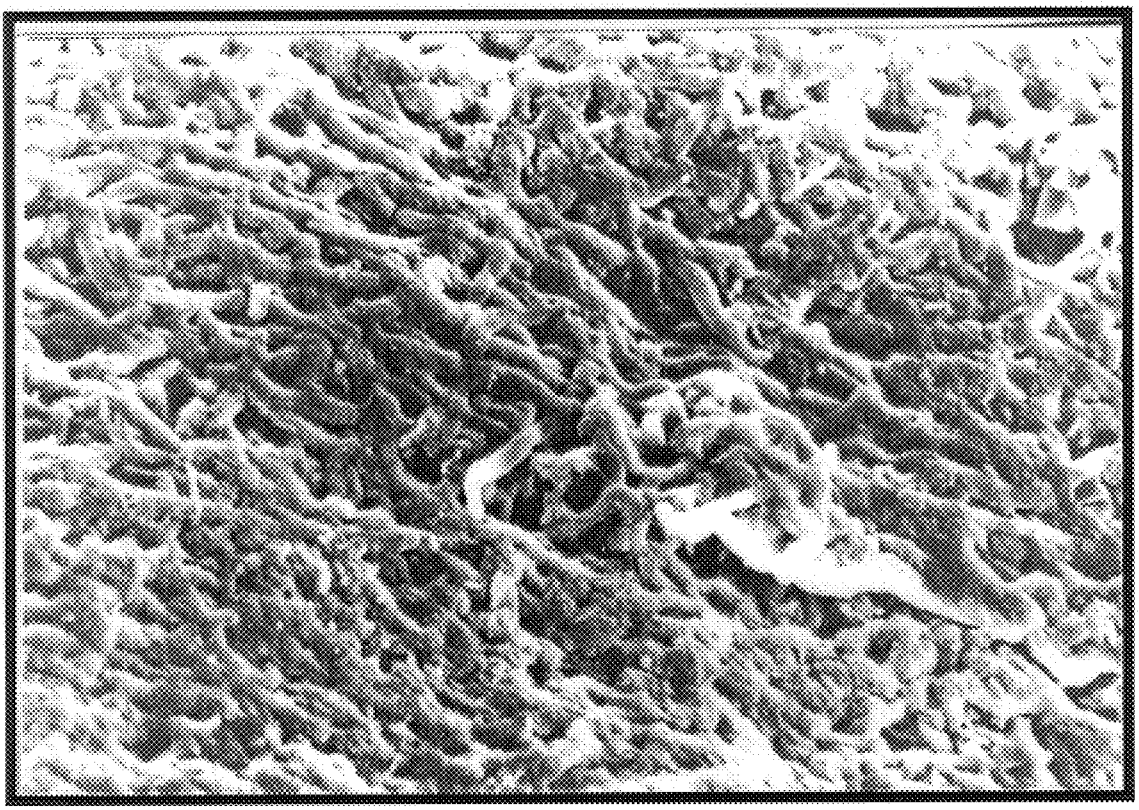
FIG. 3 shows a surface of submerged culture pellet of *Pleurotus ostreatus* CBS 101937. Scanning electron microscopy (SEM), ×1500.
Figure 4:
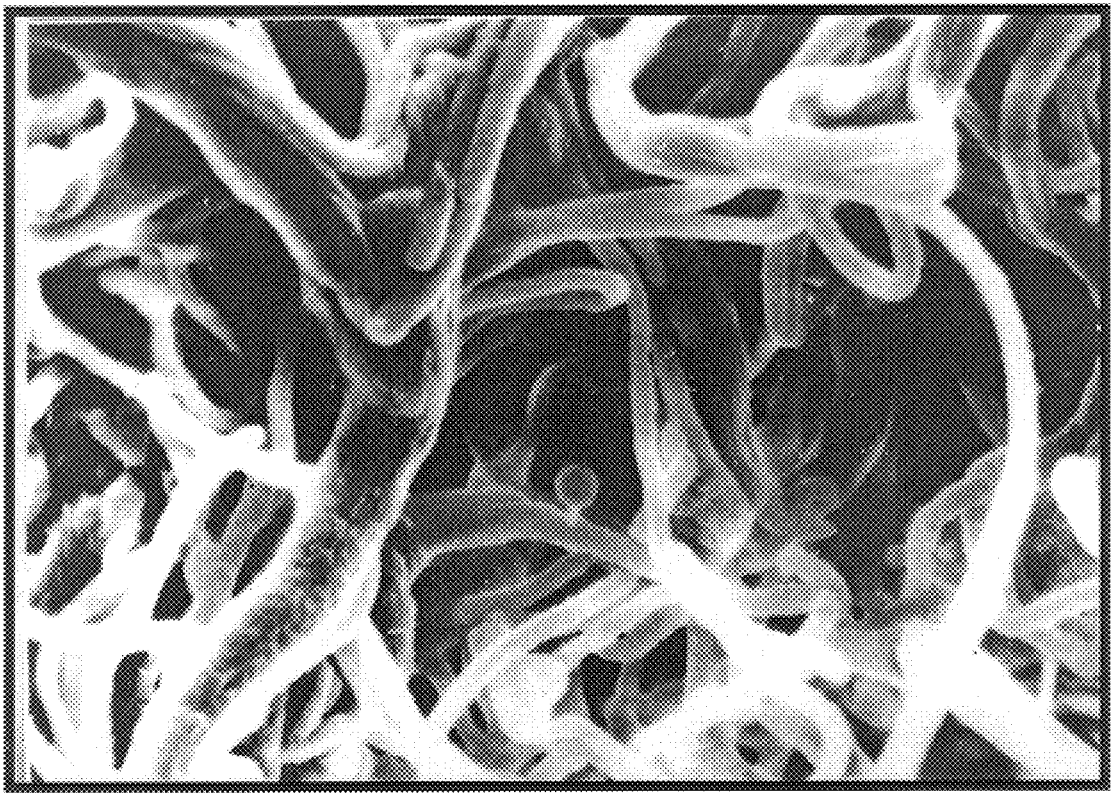
FIG. 4 shows a part of a surface of submerged culture pellet of *Pleurotus ostreatus* CBS 101937. SEM, ×3000.
Figure 5:
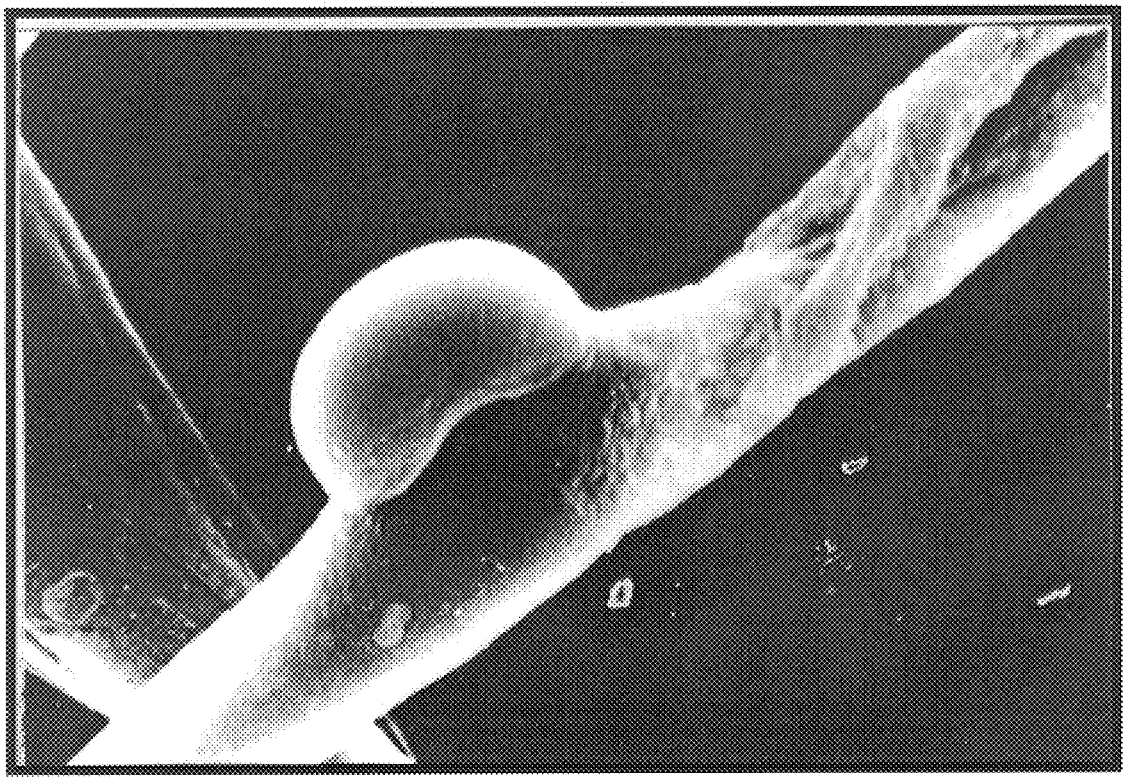
FIG. 5 shows a single clamp connection on a hypha of *Pleurotus ostreatus* CBS 101937, typical for Basidiomycetes. SEM, ×4000.
Figure 6:
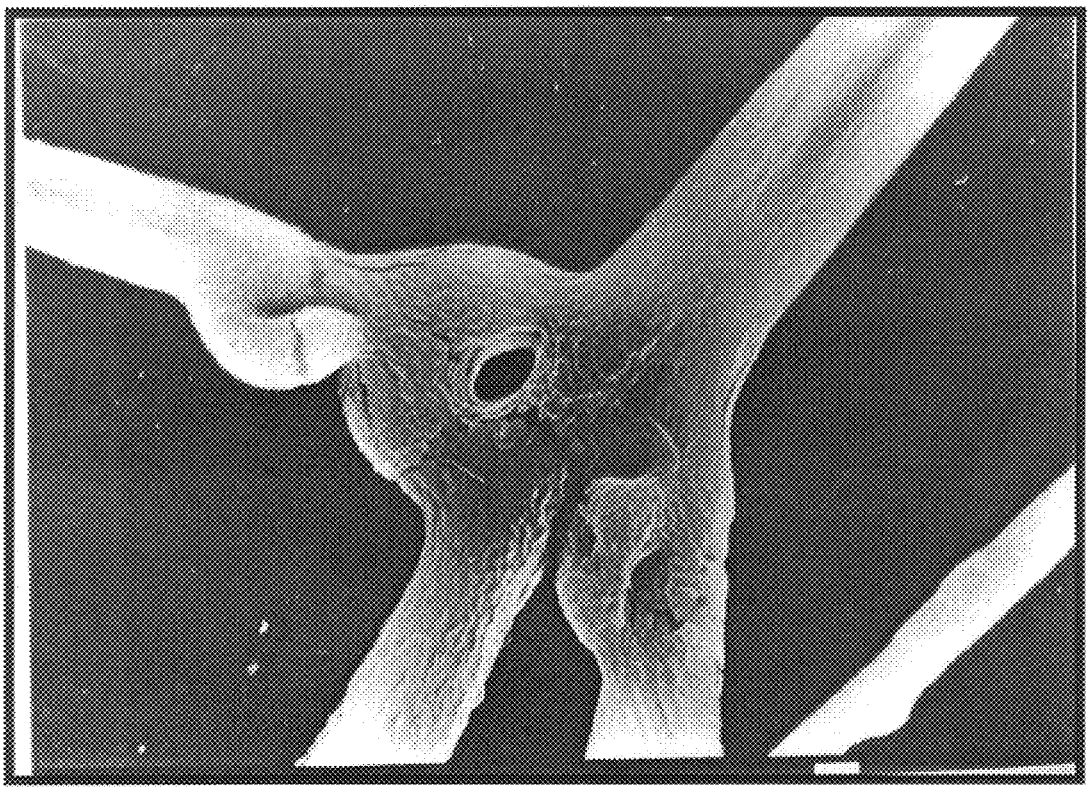
FIG. 6 shows a clamp connection on a *Pleurotus ostreatus* CBS 101937 hypha proliferating by new hyphae with clamps. SEM, ×4800.
Figure 7:
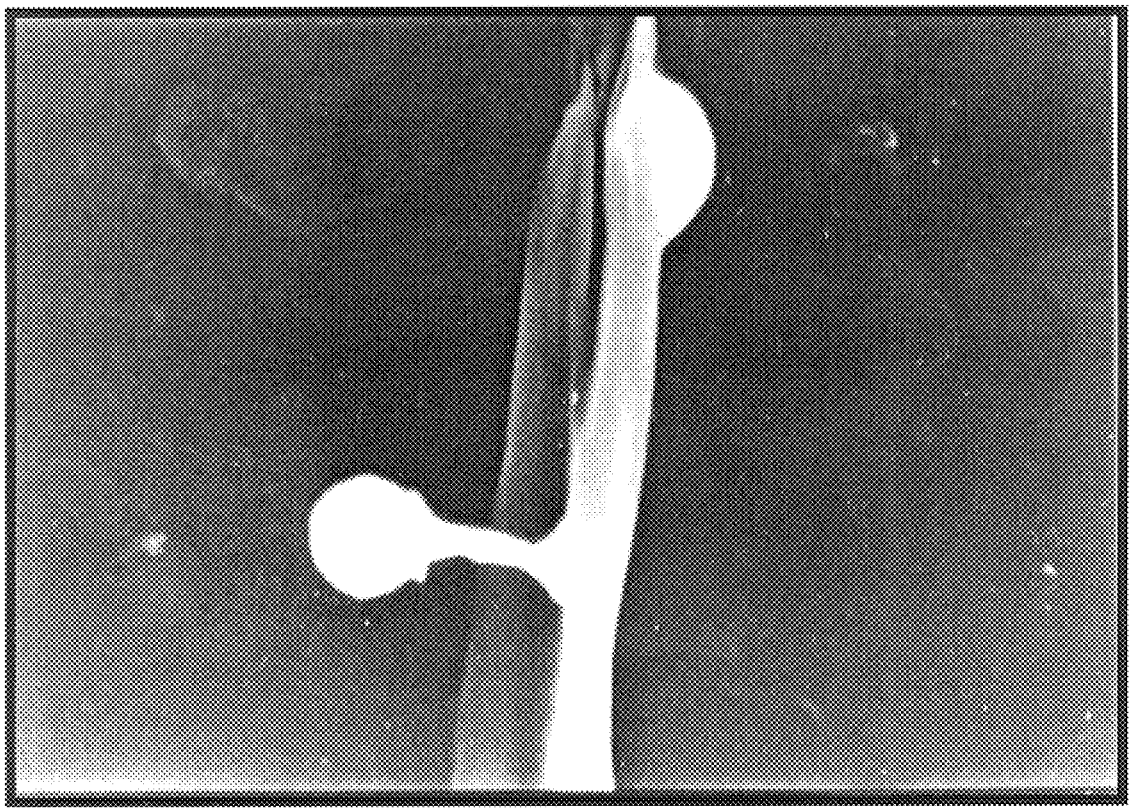
FIG. 7 shows a conidium-like structure on a hypha of *Pleurotus ostreatus* CBS 1101937, a typical for the genus Pleurotus. SEM, ×6000.
Figure 8:
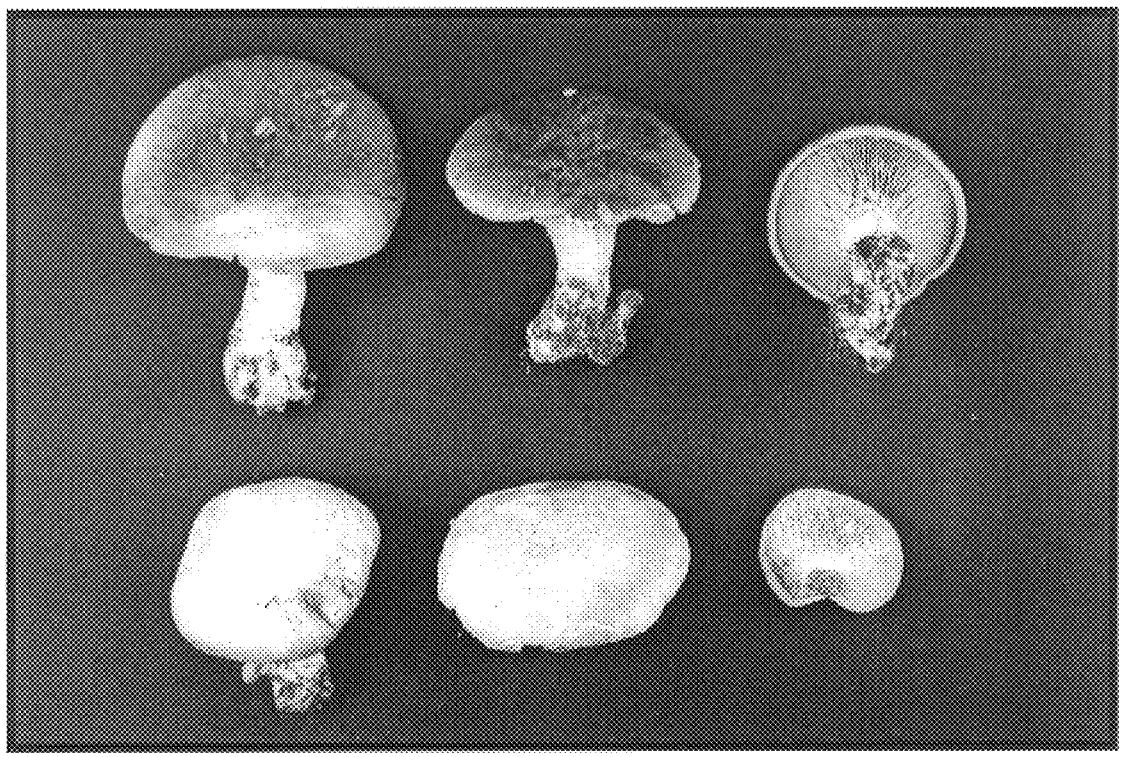
FIG. 8 shows a top view of the *Pleurotus eryngii* var. *ferulae* fruiting bodies.
Figure 9:
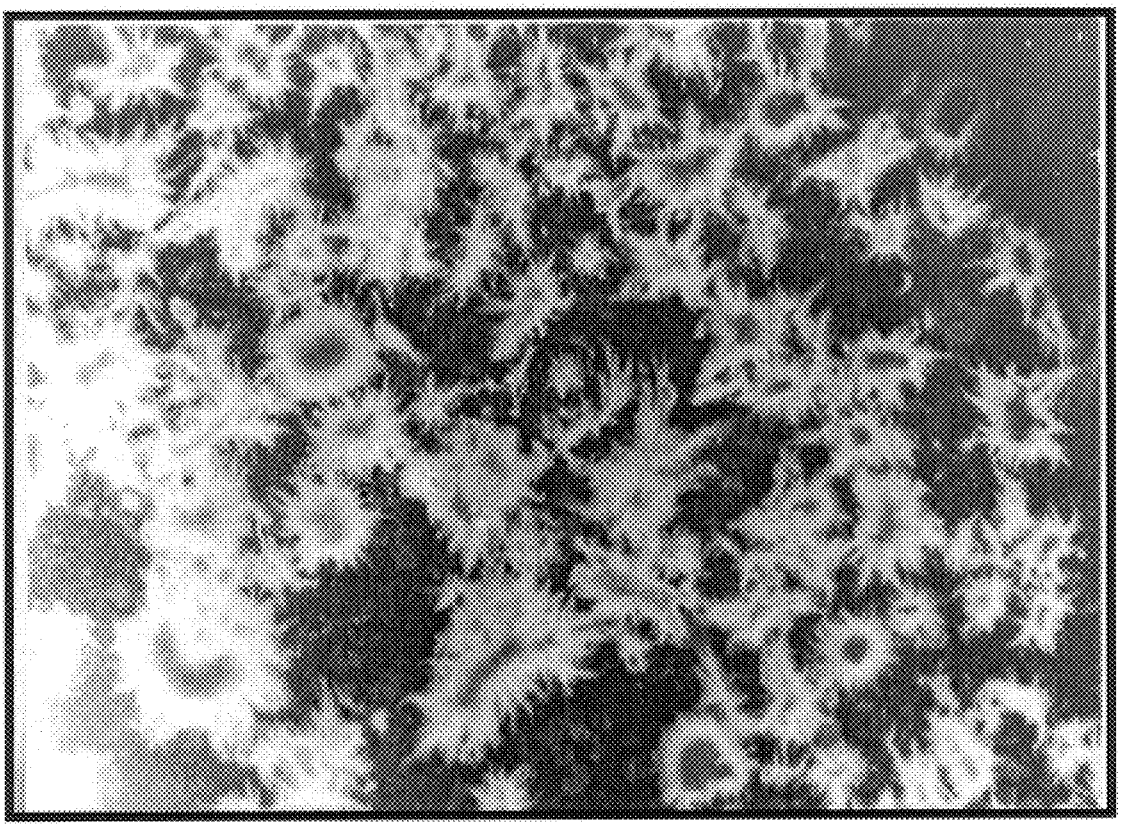
FIG. 9 shows a view of *Pleurotus eryngii* var. *ferulae* CBS 101938 submerged culture biomass in the form of pellets. Magnification ×10.
Figure 10:
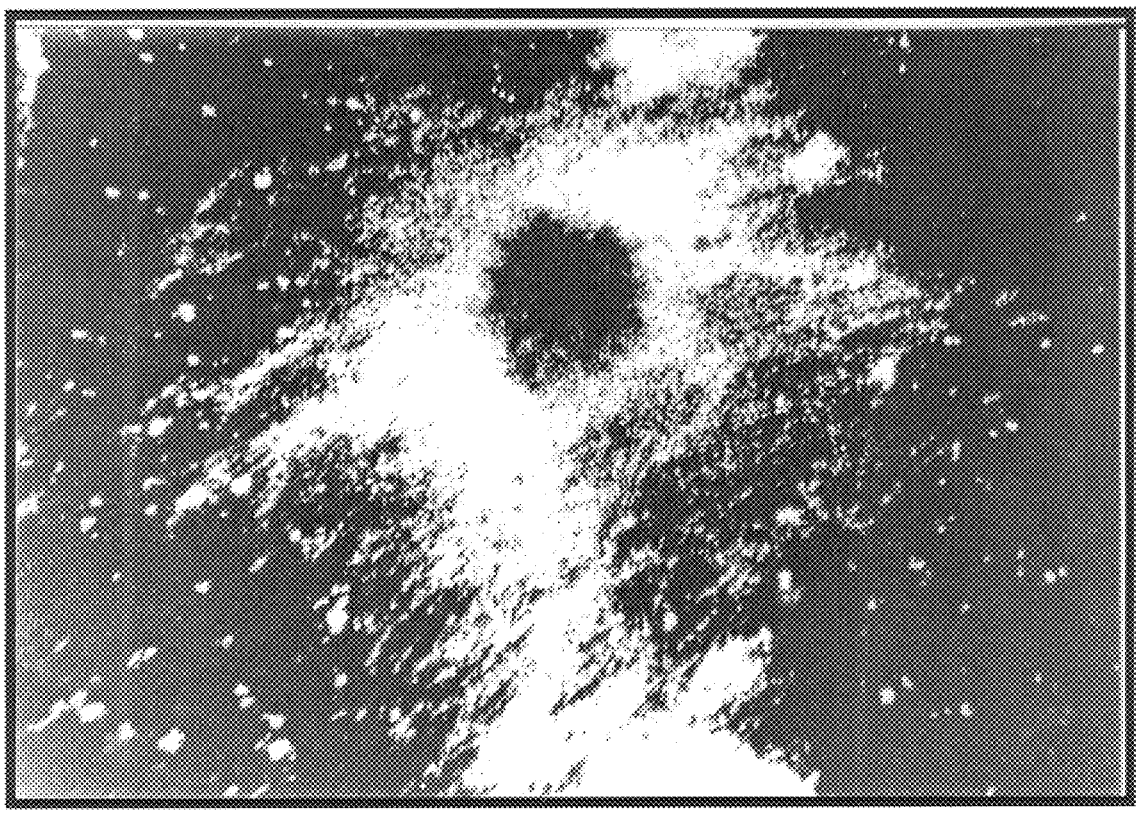
FIG. 10 shows a view of *Pleurotus eryngii* var. *ferulae* BS 101938 submerged culture biomass in the form of pellets. Magnification ×40.
Figure 11:
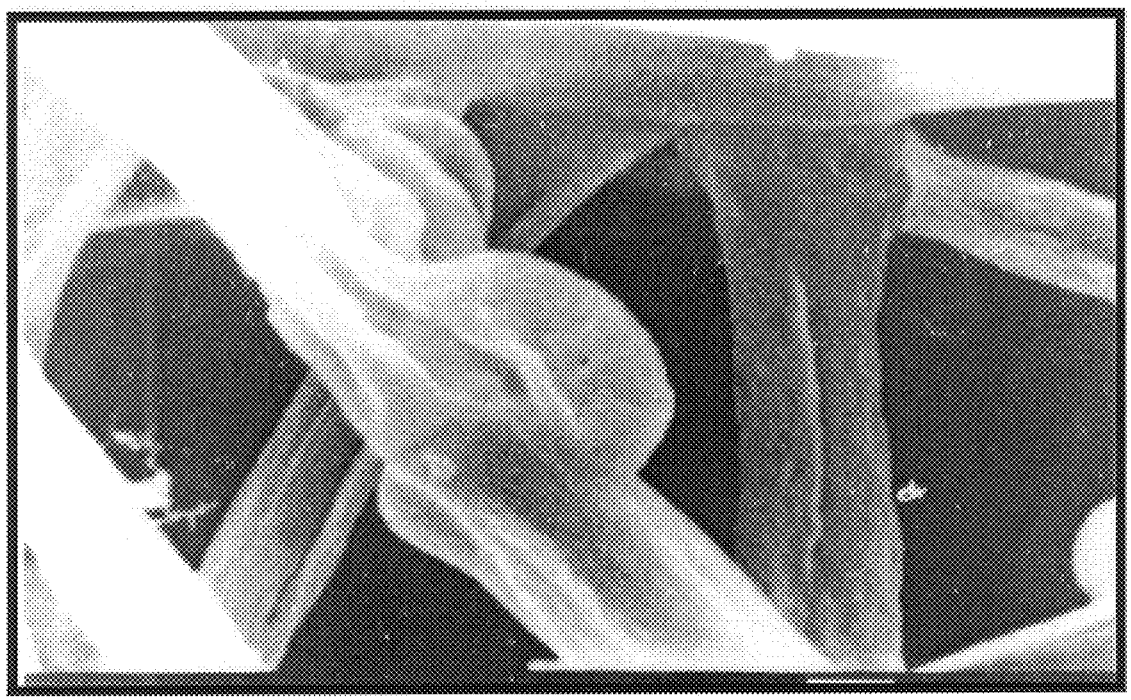
FIG. 11 shows a single clamp connection on a hypha of *Pleurotus eryngii* var. *ferulae* CBS 101938, typical for Basidiomycetes. SEM, ×7800.
Figure 12:
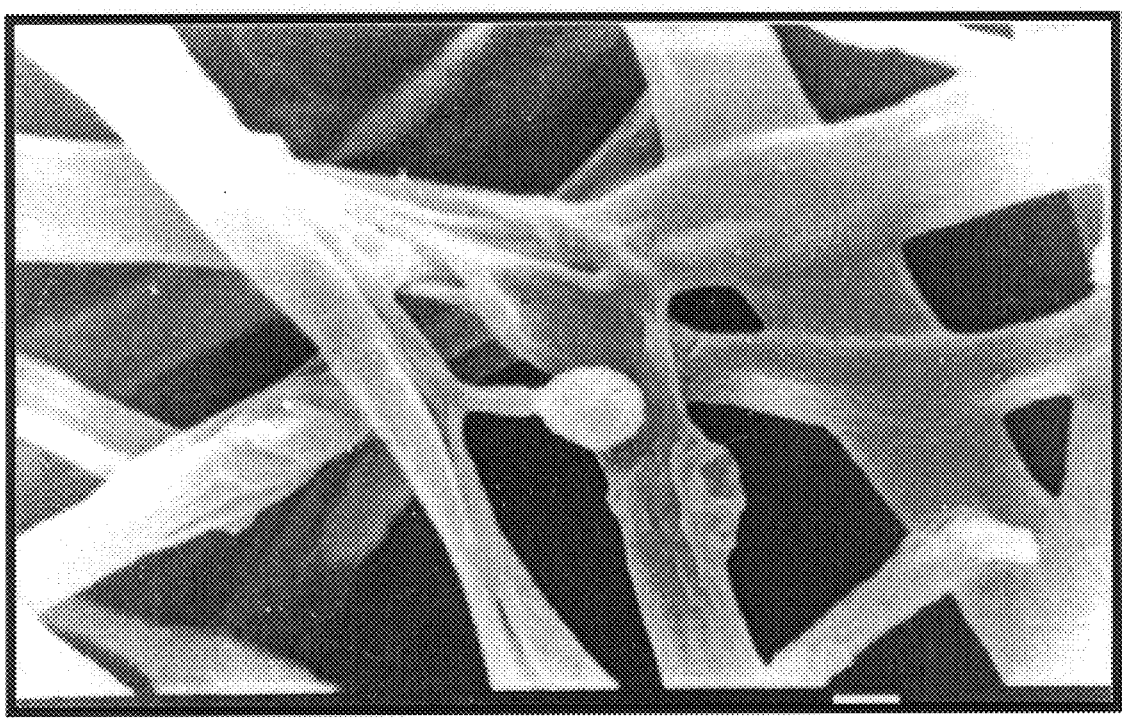
FIG. 12 shows a conidium-like structure on a hypha of *Pleurotus eryngii* var. *ferulae* BS 101938, typical for the genus Pleurotus. SEM, ×6000.

An object of the present invention was to overcome the deficiencies of the state of the art and to provide: i) a process for producing cholesterol-lowering compounds in an efficient and economic way, and ii) in a nutriceutical composition that is edible and useful as a dietary supplement.

PROCESS FOR PRODUCTION OF AN EDIBLE BASIDIOMYCETES NUTRICEUTICAL

A process according to the invention comprises the submerged cultivation of edible higher Basidiomycetes mushrooms, producers of lovastatin, belonging to the genus Pleurotus on a nutrient media including nitrogen, mineral salts and a source of carbon - mono- or polysaccharides including glucose; one-step isolation procedure from a fermentation broth obtained from the submerged culture and a method of preparing a hypocholesterolemic, hypolipidemic, protein, or mineral functional food.

The field of this invention relates to edible higher Basidiomycetes mushrooms from the genus Pleurotus and a process for culturing them for the production of a biomass with a high concentration of lovastatin, as a dietary supplement with hypocholesterolemic activity, which is suitable for human consumption.

Hypercholesterolemia is one of the main risk factors of cardiovascular disease, causing high blood pressure and atherosclerosis. So many efforts have been made to find methods or substances which would reduce cholesterol uptake from the digestive tract, or destroy cholesterol by enzyme reactions. The most practical way to protect the human body from high cholesterol levels is to inhibit the cholesterol-synthesizing ability of an organism.

One of the best known hypocholesterolemic pharmacological agents of natural origin, which is the competitive inhibitor of 3-hydroxy-3-methylglutaryl-coenzyme A reductase (HMG CoA reductase)—the key enzyme in cholesterol metabolism—is lovastatin (mevinolin, MSD 803), described by Monaghan et al. (U.S. Pat. No. 4,231,938).

Mevinolin contains a naphthalene ring system, a 0-hydroxy lactone and a methylbutyric acid. It belongs to the series of similar compounds such as ML-236, compactin, monacolin K. These compounds are metabolites of mold fungi from the genera Aspergillus, Penicillium, Eupenicillium, Paecilomyces, Trichoderma, Phoma, Hypomyces, Pythium, Doratomyces and Gymnoascus. Later, the presence of lovastatin was detected in a submerged culture of three higher Basidiomycetes species: *Pleurotus ostreatus, P. saca* and *P. sapidus*. The discovery of lovastatin in fruit bodies of *P. ostreatus* helps to interpret the hypocholesterolemic activity of Pleurotus fruit body preparations previously described in a series of experiments. It was found that addition of 2 to 4% of *P. ostreatus* fruit bodies to the hyperlipidemic diet efficiently prevented accumulation of cholesterol and triacylglycerols in both sera and liver of rats with experimentally or genetically induced hyperlipidemia. This effect was attributed to the fiber pulp complex of the *P. ostreatus* mushroom, which limits the absorption of cholesterol in the gastrointestinal tract. Later it was found that a 30% ethanol extract of *P. ostreatus* is equivalent in activity to a whole oyster mushroom and suggested that this effect may be related to the lovastatin content in the fruit bodies. Bobek et al., 1996, Nährung: 222–224.

When fruiting bodies of the edible and commercially available mushroom Pleurotus ostreatus were investigated, it was found that they contained significant amounts of lovastatin, which varies in quantity when obtained from submerged or surface fermented different Pleurotus strains. Moreover, the lovastatin content in fruit bodies of *P. ostreatus* is not constant even in the same strain and depends mainly on substrate variability, on fruit body size and age, and is concentrated presumably in the lamellae and basidiospores but not in stipe or cap tissue.

The best producers of lovastatin are different strains of *Aspergillus terreus*, a common contaminant mold on food, possessing such toxic metabolites as terrein, patulin, citrinin, and citreoviridin. This leads to the necessary purification of lovastatin from other Aspergillus secondary metabolites. As described in U.S. Pat. No. 4,231,938, the purification process includes extraction of lovastatin from the culture broth with ethyl acetate or XAD-2 resin and the subsequent procedure of concentration, washing, reconcentration and crystallization. Some other proposed processes for isolation of lovastatin differ by the use of a more selective resin (EP 877089 A1) or of less toxic solvent butyl acetate in the first step of extraction (U.S. Pat. No. 5,712,130), but all these modified processes deal with the extraction procedure of the whole culture broth including both culture medium and cell biomass.

A process for extraction lovastatin from the submerged culture broth of *Pleurotus ostreatus, P. sapidus* and *P. saca* was proposed by adding an equal volume of methanol. The final product is extracted by shaking the culture broth with methanol, separating the mycelium by filtering, and obtaining the lovastatin in the lactone or acid form depending from the previous adjustment pH of the culture broth to 3,0 or 7,7 (DE Pat. 440259).

The general efficiency of processes for lovastatin production is determined by the productivity of fungi strains and the number of steps in the extraction procedure. Aspergillus strains are more productive than those of Pleurotus, but they produce a wide range of toxic substances, beside lovastatin, and involve complex extraction methods for lovastatin purification.

Although such methods are certainly appraised as rational and practical, they still involve extraction processes of large volumes of culture broth by solvents of different toxicity.

The strains of Pleurotus used in the present invention were obtained from the growing fruit bodies collected in Israel by a tissue-culture method. Pieces of cap tissue were put onto malt extract agar, pH-6.3 and incubated at 27° C. The morphological characteristics of obtained cultures were typical of Basidiomycetes by the presence of clamp connections at each septa.

Using the criteria specified for fruit bodies in the standard authority "The genus Pleurotus (Fr.) Kummer (2)", Oswald Hilber, published in 1997, and by comparison with known species, they were determined as *Pleurotus ostreatus* (Jacq. : Fr.) Kumm and *Pleurotus eryngii* (DC. : Fr.) Quél. var. *ferulae* Lanzi respectively. According to the Budapest Treaty on the international recognition of the deposit of microorganisms for purposes of patent procedure two strains were deposited in the Centraalbureau voor Schimmelcultures, Netherlands:

| Species | Dep. No | Dep. Date |
| --- | --- | --- |
| *Pleurotus ostreatus* (Jacq. Fr.) Kumm. | CBS 101937 | June 14, 1999 |
| *Pleurotus eryngii* (DC.: Fr.) Quél. Var. *ferulae* Lanzi | CBS 101938 | June 14, 1999 |

All species of the genus Pleurotus are edible, and some of them, especially *P. ostreatus, P. pulmonarius (=P. sajor-caju)* and related species are commercially cultivated.

The culture of these strains to produce lovastatin is carried out in aqueous media such as those employed for good mycelium growth and biomass accumulation. Such media contain sources of carbon, nitrogen and inorganic salts assimilated by the growing culture.

All species of genus Pleurotus are capable to utilize lignocellulose materials, so a wide range of carbohydrates including pentoses, hexoses and polysaccharides are good sources of carbon for their growth. Glucose, sucrose and starches such as grain, corn meal and the like are the main ingredients that can be used either alone or in combination as sources of carbon. The amount of carbohydrate usually varies between about 3% and 5% by weight of the medium to provide a high yield of biomass.

The best sources of nitrogen possessing it in organic form include yeast hydrolysates or extract, bacteriological peptone, corn steep liquor and the like. The sources of nitrogen either alone or in combination are used in the range of 0.5% to 4% by weight depending on N content in the source, but about I to 1.5 g of pure N per liter of culture medium.

Among inorganic salts, which can be incorporated in the culture media are salts possessing cations of potassium, ammonium and magnesium. Sodium is not needed for growth at all. Useful cations can be obtained in the form of phosphate, or sulfate and chloride. The main microelements Fe, Mn, Zn and Cu are available from any type of inorganic salts.

The fermentation is carried out at temperatures ranging from 20° C. to 28° C. The optimal temperature for growth in a refrigerated orbital incubator is 27° C., and 28° C. is maximal; further increase of temperature is detrimental and at 30° C. Pleurotus mycelium of the foregoing species stopped its growth.

Lovastatin is produced by both surface and submerged culture. However, in surface culture at stationary conditions of growth on a liquid medium the lovastatin content did not reach a maximum value that is expected for this type of a medium. Hence, the surface method of cultivation can be used only for screening for lovastatin producing strains.

The fermentation in submerged culture includes one or more stages of seed development under controlled conditions. The liquid nutrient medium for the first step of inoculum preparation may be any suitable combination of carbon and nitrogen sources, preferably glucose or sucrose, and peptone or yeast extract. The inoculum flask inoculated from surface agar culture (tube or Petri dish) was kept at stationary conditions of growth in a constant temperature chamber at about 27° C. until the mycelium mat covered all the surface of the medium. Then the mycelium mat was transferred to the sterile vessel of a waring commercial laboratory blender with water and homogenized at a low speed setting. Ten milliliters of mycelium homogenate was transferred to 100 ml of sterile medium and the seed flask was shaken 6–7 days at 100–120 rpm until growth is satisfactory in the form of pulp. The seed flask content was transferred to 1 l of sterile medium for the fermentation process, so the two-step seed development included the scaling process of transferring inoculum to pure medium in the proportion 1:10.

The following examples are provided to illustrate and in no way limit the scope of the process of the present invention and should not be construed as being limiting.

EXAMPLE 1

A. Fermentation

A tube with a 8–10 days old pure culture of *Pleurotus eryngii* var. *ferulae* CBS 101938 on malt agar pH 6.2 was used for inoculation into 100 ml of medium A in a 250 ml Erlemneyer flask (inoculum flask). Medium A has the following composition (g/l):

| Medium A | |
|---|---|
| Glucose (Dextrose) | 25 |
| Peptone | 2 |
| Yeast extract | 1 |
| $KH_2PO_4$ | 0.5 |
| $MgSO_4.7H_2O$ | 0.25 |
| $CaCl_2.2H_2O$ | 0.1 |
| Corn Steep Liquor | 2.5 ml |
| Trace Element Mixture | 10 ml |
| 10% KOH | 2.5 ml |
| Trace Element Mixture (g/l): | |
| $FeSO_4.7H_2O$ | 0.5 |
| $MnSO_4.H_2O$ | 0.1 |
| $ZnSO_4.7H_2O$ | 0.05 |
| $CuSO_4.5H_2O$ | 0.02 |

After 30 min. of sterilization at 120° C., pH of the medium A is between 6.2 to 6.5.

The inoculated flasks were incubated at stationary conditions of growth in a temperature chamber at 27° C. After 6–8 days of growth a mycelium mat which covered all the surface of the culture medium was placed into the sterile vessel of a waring commercial laboratory blender, 100 ml of sterile water added and the mycelium homogenized at a low speed setting during 30 seconds.

New 250 ml Erlenmeyer flasks with 100 ml of sterile medium A were each inoculated with 10 ml of mycelium homogenate (seed flasks) and incubated in the refrigerated orbital incubator at 120 rpm, 27° C. for 6 days.

The seed flask content (100 ml of pulp biomass) was used to inoculate 1000 ml of medium B in two-liter Erlemneyer flasks and the fermentation process was carried out at 27° C. on a 120 rpm shaker. Medium B has the following composition (g/l):

| Medium B | |
|---|---|
| Glucose (Dextrose) | 50 |
| Peptone | 0.5 |
| Yeast extract | 1 |
| $(NH_4)_2SO_4$ | 2 |
| $K_2HPO_4.3H_2O$ | 2 |
| $K_2HPO_4$ | 2.5 |
| Trace Element Mixture | 10 ml |
| Trace Element Mixture (g/l): | |
| $FeSO_4.7H_2O$ | 0.5 g |
| $MnSO_4.H_2O$ | 0.1 |
| $ZnSO_4.7H_2O$ | 0.05 |
| $CuSO_4.5H_2O$ | 0.02 |

After 30 min. of sterilization at 120° C., pH of the medium B is between 6.2 to 6.5.

B. Testing of lovastatin

The incubated broth was filtered through a filter cloth to remove the mycelium and washed twice with distilled water. Fresh mycelium (10 g) was disintegrated in 40 ml of water on a Virtis Gardiner laboratory homogenizer and 30 ml of homogenate taken for preparation of samples, while 10 ml was used to estimate the dry weight of the biomass.

Dry submerged mycelium samples were ground into a powder of which 0.5 g was presoaked in 30 ml of distilled water using a magnetic stirrer for 30 min. The sample pH was adjusted to 7.7 using 4% NaOH, then 5 ml of methanol and 10 ml of ethyl acetate for UPLC (Carlo Erba) were added. The extraction process in the two-phase solvent system H20:MeOH:ethyl acetate—3:0.5:1 was performed on a magnetic stirrer for 30 min. This was followed by centrifugation at 5000 rpm and 4° C. for 10 min and a probe from the upper ethyl acetate layer was taken for HPLC analysis using a Meta Chem nylon syringe filter of 0.45 u pore size (Part No. 4104).

The same extraction process was done with culture broth filtrate after separation from the mycelium. The samples were analyzed on an HPLC Meta Chem Inertsil $5\mu$ ODS-2 250×4.6 min column using 0.05 M sodium phosphate pH 3.0:acetonitrile (45:55, v/v) (Monaghan et al., 1980) at a flow rate of I ml/min. at 25° C. as the eluent. A 655 A Hitachi UV detector set at 237 nm was used for lovastatin detection. Standard samples were prepared by dissolving Mevacor tablets (Merk) in water: MeOH: ethyl acetate (3:05:1, v/v) at pH 7.7.

Lovastatin content in the submerged myceliurn was determined at different stages of culture growth (Table 1).

TABLE 1

| Time of growth, days | Biomass, g/l dry weight | Lovastatin, mg/g, dry biomass |
|---|---|---|
| 6 | 3.95 | 0.46 |
| 8 | 7.76 | 0.41 |
| 10 | 8.56 | 0.52 |
| 12 | 12.20 | 0.41 |

It was found that lovastatin content in *P. eryngii* var. *ferulae* CBS 101938 submerged mycelium is stable during all phases of growth. No lovastatin was detected in the culture broth filtrate samples after separation from the mycelium. biomass.

EXAMPLE 2

A. Fermentation

A tube with a 8–10 days old pure culture of *Pleurotus eryngii* var. *ferulae* CBS 101938 on malt agar pH 6.2 was used for inoculating of 100 ml of medium A in a 250 ml Erlenmeyer flask (inoculum flask). Medium A has the following composition (g/l):

| Medium A | |
|---|---|
| Glucose (Dextrose) | 25 |
| Peptone | 0.5 |
| Yeast extract | 1 |
| $KH_2HPO_4$ | 0.5 |
| $MgSO_4.7H_2O$ | 0.25 |
| $CaCl_2.2H_2O$ | 0.1 |
| Corn Steep liquor | 10 ml |
| Trace Element Mixture | 10 ml |
| 10% KOH | 2.5 ml |
| Trace Element Mixture (g/l): | |
| $FeSO_4.7H_2O$ | 0.5 |
| $MnSO_4.H_2O$ | 0.1 |
| $ZnSO_4.7H_2O$ | 0.05 |
| $CuSO_4.5H_2O$ | 0.02 |

After 30 min. of sterilization at 120° C., pH of the medium A is between 6.2 to 6.5.

The inoculated flasks were incubated at stationary conditions of growth in a temperature chamber at 27 C. After 6–8 days of growth a mycelium mat which covered all the surface of the culture medium was placed into a sterile vessel of Waring commercial laboratory blender, 100 ml of sterile water was added and the mycelium homogenized at low speed setting during 30 seconds.

New 250 ml Erlenmeyer flasks with 100 ml of sterile medium A were each inoculated with 10 ml of mycelium homogenate (seed flasks) and incubated in the refrigerated orbital incubator at 120 rpm, 27° C. during 6 days.

The seed flask content (100 ml of pulp biomass) was used to inoculate 1000 ml of medium A in two-liter Erlenmeyer flasks and the fermentation process was carried out at 27° C. on a 120 rpm shaker.

B. Testing of lovastatin

Lovastatin content in the submerged mycelium was determined according to the method described in Example 1.

Lovastatin content in the submerged mycelium was determined at different stages of culture growth (Table 2).

TABLE 2

| Time of growth, days | Biomass, g/l dry weight | Lovastatin, mg/g, dry biomass |
|---|---|---|
| 6 | 10.11 | 0.1 |
| 8 | 11.23 | 0.24 |

Lovastatin synthesis by *P. eryngii* var. *ferulae* CBS 101938 on the fermentation medium A is lower than the same strain on the fermentation medium B (Example 1). However, it is a characteristic feature of this strain on a culture medium, which can provide a good yield of biomass, about 10 g/l dry weight.

No lovastatin was detected in the culture broth filtrate samples after separation from the mycelium biomass.

EXAMPLE 3

A. Fermentation

A tube with a 8–10 days old pure culture of *Pleurotus ostreatus* CBS 101937 on malt agar pH 6.2 was used for inoculating into 100 ml of medium A in a 250 ml Erlenmeyer flask (inoculum flask). Medium A has the following composition (g/l):

| Medium A | |
|---|---|
| Glucose (Dextrose) | 25 |
| Peptone | 2 |
| Yeast extract | 1 |
| $KH_2PO_4$ | 0.5 |
| $MgSO_4.7H_2O$ | 0.25 |
| $CaCl_2.2H_2O$ | 0.1 |
| Corn Steep liquor | 2.5 ml |
| Trace Element Mixture | 10 ml |
| 10% KOH | 2.5 ml |
| Trace Element Mixture (g/l): | |
| $FeSO_4.7H_2O$ | 0.5 |
| $MnSO_4.7H_2O$ | 0.5 |
| $ZnSO_4.7H_2O$ | 0.05 |
| $CuSO_4.7H_2O$ | 0.02 |

After 30 min. of sterilization at 120° C., pH of the medium A is between 6.2 to 6.5.

The inoculated flasks were incubated at stationary conditions of growth in a temperature chamber at 27° C. After 6–8 days of growth a mycelium mat which covered all the surface of the culture medium was placed into the sterile vessel of a waring commercial laboratory blender, 100 ml of sterile water was added and the mycelium homogenized at a low speed setting during 30 seconds.

New 250 ml Erlemneyer flasks with 100 ml of sterile medium A were each inoculated with 10 ml of mycelium homogenate (seed flasks) and incubated in the refrigerated orbital incubator at 120 rpm, 27° C. during 6 days.

The seed flask content (100 ml of pulp biomass) was used to inoculate 1000 ml of medium B in two-liter Erlenmeyer flasks and the fermentation process was carried out at 27° C. on a 120 rpm shaker. Medium B has the following composition (g/l):

| Medium B | |
|---|---|
| Glucose (Dextrose) | 50 |
| Peptone | 0.5 |
| Yeast extract | 1 |
| $(NH_4)SO_4$ | 2 |
| $K_2HPO_4.3H_2O$ | 2 |
| $KH_2PO_4$ | 2.5 |
| Trace Element Mixture | 10 ml |
| Trace Element Mixture (g/l): | |
| $FeSO_4.7H_2O$ | 0.5 |
| $MnSO_4.7H_2O$ | 0.1 |
| $ZnSO_4.7H_2O$ | 0.05 |
| $CuSO_4.7H_2O$ | 0.02 |

After 30 min. of sterilization at 120° C., pH of the medium B is between 6.2 to 6.5.

B. Testing of lovastatin

Lovastatin content in the submerged myceliurn was determined according to the method described in Example 1.

Lovastatin content in the submerged mycelium was determined at different stages of culture growth (Table 3).

TABLE 3

| Time of growth, days | Biomass, g/l dry weight | Lovastatin, mg/g, dry biomass |
|---|---|---|
| 6 | 3.65 | 0.44 |
| 8 | 9.30 | 0.23 |
| 10 | 9.30 | 0.20 |
| 12 | 5.50 | 0.15 |

It was found that the maximum accumulation of lovastatin in *Pleurotus ostreatus* CBS 101937 mycelium is related to the exponential stage of growth, with accumulation being somewhat less at the beginning and during the stationary stage.

No lovastatin was detected in the culture broth filtrate samples after separation from the myceliurn biomass.

EXAMPLE 4

Lovastatin is known to be stable in pure solutions, for example its concentrate in toluene completed lactonisation at 106° C. for 2 hours (U.S. Pat. No. 5,712,130). However, the stability of lovastatin found in the fresh biomass of mushroom, and the effect of the drying procedure used were not known. By carrying out a series of tests under different conditions, it was found that the stability of lovastatin in the biomass was temperature sensitive. Therefore, low temperatures are recommended in general for drying processes of composite biological material in order not to destroy many biologically active compounds.

Samples of *Pleurotus eryngii* var. *ferulae* CBS 101938 submerged mycelium obtained according to the process described in example 1 were pretreated before the extraction procedure for lovastatin determination at different temperatures (Table 4).

TABLE 4

| Sample | Treatment | Lovastatin, mg/g, dry biomass |
|---|---|---|
| *Pleurotus eryngii* var. *feruale* CBS 101938 6 days on medium B, example 1 | 40° C. | 0.46 |
| | 45° C. | 0.45 |
| | 90° C. | 0.18 |

Therefore, the temperature for the drying process of submerged Pleurotus mycelium should not be higher than 45° C. Low extraction of lovastatin after high-temperature treatment may be due not only to destruction of its molecule but to the attachment to denatured biopolymers. This process can lead to a weak absorption of lovastatin in the digestive tract from the denatured mycelium biomass.

NUTRICEUTICAL FORMULATIONS AND BIOCHEMICAL COMPOSITION

Nutriceutical compositions containing cholesterol-lowering compounds must be stable under the conditions of manufacture and storage and may be protected from contamination by microorganisms, such as fungi and bacteria, through the use of bacteriostatic agents, antioxidants such as vitamin E and ethoxyquin, which are listed as generally safe for use by the Food and Drug Administration.

The cholesterol-lowering compound can be used to reduce the blood levels of cholesterol and for the treatment of hyperlipidemias including hypercholesterolemia and associated disease states such atherosclerosis, cardiovascular disease and pancreatitis. The cholesterol-lowering compound can also be used in normal subjects as a preventative measure to prevent the occurrence of these disorders. It is desirable that human serum cholesterol levels be maintained below 180 mg/dl, with values of 240 mg being considered clinically high and values of 160 mg being considered too low.

The formulation is taken as a single daily dose or divided daily doses, most preferably three doses given before, during or after meals. Patients can be maintained on cholesterol-lowering compounds indefinitely to regulate the synthesis of cholesterol by the liver. Conditions to be considered in selecting dosage level, frequency, and duration primarily include the severity of the patient's disorder, the patient's serum cholesterol level, adverse side effects and the patient's need for preventive intervention as well as the therapeutic efficacy. It is to be understood that for any particular subject, specific dosage regimens should be adjusted over time according to the individual patient's need and the professional judgment of the person administering or supervising the administration of the nutriceutical compositions, and that the concentration ranges set forth herein are exemplary only and are not intended to limit the scope or practice of the claimed composition. Other concentration ranges and dosage durations can be determined by routine experimentation.

Table 5 describes the general composition of the *P. ostreatus* CBS 101937 submerged mycelium (% dry weight), specifically for carbohydrates, crude fiber, crude protein, lipids and ash.

TABLE 5

| General nutrients | Mycelium |
|---|---|
| Total carbohydrate | 41.0–58.0 |
| Crude fiber | 5.0–5.8 |
| Crude protein | 21.0–48.0 |
| Total lipids | 2.0–7.2 |
| Ash | 4.2–7.9 |

Table 6 describes the protein and amino acid composition of the *P. ostreatus* CBS 101937 submerged mycelium (g/100 g crude protein)

TABLE 6

| Amino Acids | Mycelium |
|---|---|
| Crude Protein (% dry weight) | 35.3–42.0 |
| Tryptophan | 0.7–0.8 |
| Lysine | 4.6–7.0 |
| Threonine | 3.1–3.5 |
| Valine | 3.0–4.5 |
| Isoleucine | 2.1–3.7 |
| Leucine | 2.9–6.3 |
| Methionine | 2.9–6.3 |
| Cysteine | 0.6–0.8 |
| Tyrosine | 1.3–2.5 |
| Phenylalanine | 2.1–2.8 |
| Total essential Amino acids | 21.0–44.0 |
| Histidine | 2.0–3.3 |
| Arginine | 3.8–6.4 |
| Aspartic acid | 6.1–7.1 |
| Serine | 2.8–4.3 |
| Glutamatic acid | 10.0–15.7 |
| Proline | 2.6–4.6 |
| Glycine | 3.4–3.8 |
| Alanine | 4.0–5.4 |
| Total amino acid | 69.0–72.0 |

Table 7 describes the Estimated Nutritive Value of *P. ostreatus* CBS 101937 submerged mycelium (M).

TABLE 7

| Protein was calculated | Protein content, % M | EAA index, (FAO) M | NI M |
|---|---|---|---|
| N total × 6.25 | 42.0 | 70.0 | 29.0 |
| N total × 4.38 | 29.0 | 99.0 | 29.0 |
| Protein | 23.0 | 125.0 | 29.0 |

Table 8 describes the fatty acid composition of the *P. ostreatus* CBS 101937 submerged mycelium (% of total methyl esters).

TABLE 8

| Fatty acid | Submerged mycelium |
|---|---|
| Myristic (14.0) | 1.5 + 0.4 |
| Palmitic (16.0) | 18.4 + 1.9 |
| Palmitoleic (16.1) | 1.5 + 0.4 |
| Oleic (18.1) | 18.4 + 1.6 |
| Linoleic (18.2) | 43.2 + 1.5 |

Table 9 describes the content of minerals in *Pleurotus ostreatus* CBS 101937 submerged mycelium (mg/100 g dry weight).

TABLE 9

| Minerals | Mycelium |
|---|---|
| Potassium | 735–1800 |
| Phosphorus | 985–1980 |
| Sodium | 80–316 |
| Calcium | 40–94 |
| Magnesium | 148–359 |
| Sulfur | 2.1 |
| Iron | 39.1–60.0 |
| Copper | 0.5–2.44 |
| Zinc | 1.85–5.70 |
| Manganese | 2.0–9.0 |
| Cobalt | 0.01–0.36 |
| Molybdenum | 0.01–0.36 |
| Selenium ($\mu$g) | 0.02–0.36 |
| Chronium | 0.05–3.4 |
| Nickel | 0.05–2.9 |
| Stannous | 7.4–31.4 |
| Vanadium | 0.01–0.02 |
| Barium | 0.03–0.15 |
| Bor | |
| Titanium | 0.15–1.3 |
| Plumbum | 0.1–0.54 |
| Silver | 0.01–0.09 |

Table 10 describes the vitamin content in *Pleurotus ostreatus* CBS 101937 submerged mycelium (mg/100 g dry weight).

TABLE 10

| | Vitamins | |
|---|---|---|
| Symbol | Compound | Mycelium |
| B1 | Thiamine | 0.6–6.0 |
| B2 | Riboflavin | 2.6–5.7 |
| B5/PP/ | Niacin | 64.0–122.0 |
| B6 | Piridoxin | 0.06–0.47 |
| B7 | Biotin ($\mu$g) | 14.0–63.0 |
| B12 | Cyanobalamin | — |
| C | Ascorbic acid | 70.0–108.0 |
| D2 | Calciferol ($\mu$g) | 0.10–0.14 |
| Pro-D | Ergosterol | — |
| E | Tocopherol | 6.6–10.6 |
| Pro-A | Beta-carotene | Trace |

The natural cholesterol-lowering nutriceuticals are generally ingested orally. However, the nutriceuticals of the present invention may be extracted further from the biomass and concentrated. These products may be administered intravenously, intraperitoneally, subcutaneously, intramuscularly, intrathecally, orally, rectally, topically or by aerosol. The present invention will further be understood with reference to the following non-limiting examples. All literature citations are expressly incorporated herein by reference.

HEALTH EFFECTS OF NUTRICEUTICAL COMPOSITIONS

Hyperlipidemias, particularly hypercholesterolemia and hyperlipoproteinemias, are risk factors for atherosclerosis. The higher the circulating levels of cholesterol, usually in the form of low density lipoproteins (LDL) containing cholesterol, the greater the risk for atherosclerosis.

Cardiovascular disease is the leading cause of death in women and middle-aged American men. Atherosclerosis, however, which is known to contribute to cardiovascular disease and stroke, begins at a much earlier age. Children and adolescents with elevated serum cholesterol levels are more likely than their counterparts with normal cholesterol levels to have parents with coronary heart disease.

Reduction of hypercholesterolemia results in a delayed onset of atherosclerosis and a decrease in progression of atherosclerosis, thus reducing the risk of coronary heart disease in humans. Specifically, relatively complicated plaques induced by hyperlipidation will regress, and progression of atherosclerosis will cease when hyper lipidemia is removed. Some forms of hyperlipidemia, including hypercholesterolemia, are potentially partially reversible with current techniques of preventive management. However, none of the current techniques is completely successful and many are associated with unwanted side effects and complications. Taking cholesterol-lowering drugs can result in a twenty percent reduction in serum cholesterol. However, drugs are not always warranted for hypercholesterolemia, and some of the hypolipemic drugs such as lovastatin, mevastatin, cholestyrmaine, clofibrate, probucol and nicotinic acid, may have serious side effects, including an increase in mortality through liver complications, or less severe side effects such as constipation, skin flushes and muscle dysfunction. Dietary therapy is usually recommended for all patients with hypercholesterolemia but is not always effective.

Accordingly, there is need for methods and compositions which are effective in lowering blood lipid levels, specifically cholesterol levels. These compositions should not in themselves have significant side effects, and would therefore be useful in treating disease states associated with high levels of blood lipids. It is therefore an object of the present inventor to provide compositions and methods of use in lowering serum cholesterol in a subject in need thereof.

Cancer is the second highest largest single cause of death in children and adults, claiming more than 6 million lives each year worldwide. Chemoprevention with agents including nonsteroidal anti-inflammatory drugs (NSAIDs) such as aspirin, ibuprofen, piroxican, indomethacin, naproxene and sulindac may be useful in reducing morbidity and mortality form cancer. Conventional NSAIDs inhibit both forms of the cyclooxygenase (COX) enzymes COX-1 and COX-2, of which COX-2 which plays a key role in cancer. Thus, in searching for new cancer chemopreventive agents, hundreds of plant extracts have been evaluated for their COX inhibitory potential. The nutriceutical compositions of the present invention, derived from edible higher Basidiomycetes mushrooms inhibit COX activity and thus have chemopreventive activity against cancer.

A large number of cellular components and secondary metabolites derived from mushrooms, have been shown to affect the immune system and are used in a variety of disease states. Mushrooms have been used as adaptogens and immunostimulants. An adaptogen as defined herein, is any substance that meets specific criteria for the category of plant derived biological response modifier, that may modify the host's biological response by a stimulation of the immune system. The principal component of these biological response modifiers is (1–>3)-$\beta$-D-glucans. $\beta$-glucan, a polysaccharide isolated from mushrooms binds to lymphocyte surfaces or serum specific proteins, which activate macrophage, T-helper, natural killer cells and other effector cells. These increase the production of antibodies as well as interleukins (IL-1, IL-2) and interferon (IFN-$\gamma$) which are released upon activation of effector cells. The carcinostatic effect of antitumor polysaccharides thus results from the activation of the host's immune system.

In addition to water-soluble $\beta$-D-glucans, mushrooms also contain $\beta$-D-glucans with heterosaccharide chains of xylose, mannose, galactose, and uronic acid, and $\beta$-D-glucan-protein complexes. The higher Basidiomycetes edible compositions grown in submerged cultures in the present invention comprised of cellular and secondary metabolites, polysaccharides and specifically β-D-glucan, and exhibit immunomodulatory and carcinostatic properties.

The higher Basidiomycetes mushrooms contain dietary fibers belonging to glucans, chitin, and heteropolysaccharides including, but not limited to, pectinous substances, hemi-celluloses or polyuronides. The P-glucans and chitinous substances are present primarily in the dietary fiber of mushrooms. Their carcinostatic activity has been attributed to their physicochemical interactions with hazardous materials such as carcinogenic substances, thereby preventing their absorption into the intestine and hastening their excretion. The higher Basidiomycetes edible compositions of the present invention comprise of dietary fibers belonging to β-glucans, chitin and heteropolysaccharides, having carcinostatic activity.

The effect of administering *Pleurotus ostreatus* CBS 101937 submerged mycelium to Wistar rats was studied in a 12-month series of experiments. Various lipid parameters and survival time were recorded.

Experimental Protocol

The experimental group consists of 500 growing Wistar rats, randomly selected, representing both male and female rats with initial body weight of about 90–110 g. Animals are kept in standard temperature conditions without regulation of light regime. A semisynthetic diet with casein albumin balanced by main food components, mineral elements and vitamins was used in the control rats.

The animals are divided into two groups: the first one received an unmodified diet (control group). The second group received food in which 0.5; 5; 10; 25 and 50% of casein were replaced by equal levels of protein from *P. ostreatus* submerged mycelium.

During the experimental period all animals were active, healthy and with normal appetite. The overall morphological characteristics did not differ between the two groups. It was found that in rats supplemented with *P. ostreatus* mycelium there was a decrease in cholesterol, triglycerides and oxidized peroxidase by-products in the blood serum and liver compared with the control group. In addition, the percentage survival in supplemented group was higher. These data indicate a hypocholoesterolemic, hypolipidemic and non-toxic effect of *P. ostreatus*. In addition, the data obtained suggest that the *P. ostreatus* submerged mycelium can be used as food additive in amount approximately equal to 5% of daily diet.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the compositions set forth without departing from the spirit and scope of the invention, it is intended that all matter contained in the above description and shown in the accompanying figures shall be interpreted as illustrative and not in a limiting sense.

It is also to be understood that the following claims are intended to cover all of the generic and specific features of the invention herein described and all statements of the scope of the invention which, as a matter of language, might be said to fall there between.

What is claimed is:

1. A proces for producing lovastatin from *P. eryngii* var. *ferulae*, said process comprising:
    a) cultivating a fungi of *P. eryngii* var. *ferulae* in a submerged culture on nutrient media at a temperature range of 25° C. to 28° C., isolating the resulting biomass of *P. eryngii* var. *ferulae* from the culture broth,
    b) drying the biomass of *P. eryngii* var. *ferulae* at a temperature range of 40° C. to 45° C., and
    c) isolating said lovastatin from said biomass.

2. The process for producing lovastatin from *P. eryngii* var. *ferulae* according to claim 1, wherein the nutrient media contains:

| Medium A | |
|---|---|
| Glucose (Dextrose) | 25 |
| Peptone | 2 |
| Yeast extract | 1 |
| $KH_2PO_4$ | 0.5 |
| $MgSO_4.7H_2O$ | 0.25 |
| $CaCl_2.2H_2O$ | 0.1 |
| Corn Steep Liquor | 2.5 ml |
| Trace Element Mixture | 10 ml |
| 10% KOH | 2.5 ml |
| Trace Element Mixture: | |
| $FeSO_4.7H_2O$ | 0.5 |
| $MnSO_4.H_2O$ | 0.1 |
| $ZnSO_4.7H_2O$ | 0.05 |
| $CuSO_4.5H_2O$ | 0.02 . |

3. The process for producing lovastatin from *P. eryngii* var. *ferulae* according to claim 1, wherein the nutrient media contains:

| Medium B | |
|---|---|
| Glucose (Dextrose) | 50 |
| Peptone | 0.5 |
| Yeast extract | 1 |
| $(NH_4)_2SO_4$ | 2 |
| $K_2HPO_4.3H_2O$ | 2 |
| $K_2HPO_4$ | 2.5 |
| Trace Element Mixture | 10 ml |
| Trace Element Mixture (g/l): | |
| $FeSO_4.7H_2O$ | 0.5 |
| $MnSO_4.H_2O$ | 0.1 |
| $ZnSO_4.7H_2O$ | 0.05 |
| $CuSO_4.5H_2O$ | 0.02 . |

4. The process for producing lovastatin from *P. eryngii* var. *ferulae* according to claim 1, wherein the *P. eryngii* var. *ferulae* is CBS101938.

* * * * *